United States Patent [19]

Dehler

[11] 4,101,828
[45] Jul. 18, 1978

[54] CORROSION DETECTOR

[75] Inventor: William H. Dehler, Wichita, Kans.

[73] Assignee: The Boeing Company, Wichita, Kans.

[21] Appl. No.: 793,403

[22] Filed: May 3, 1977

[51] Int. Cl.² .......................................... G01R 27/02
[52] U.S. Cl. ........................... 324/65 R; 324/65 CR;
324/71 R; 338/13
[58] Field of Search .............. 324/65 R, 65 P, 65 CR,
324/71 R; 338/13, 34

[56] References Cited

U.S. PATENT DOCUMENTS

| 1,573,174 | 2/1926 | Lasker, Jr. .......................... 324/65 P |
| 2,793,527 | 5/1957 | Turner, Jr. et al. ................ 324/65 P |
| 2,878,354 | 3/1959 | Ellison .................................. 338/13 |

FOREIGN PATENT DOCUMENTS

| 922,225 | 3/1963 | United Kingdom ............... 324/65 P |
| 1,206,594 | 9/1970 | United Kingdom ............... 324/65 P |

*Primary Examiner*—Stanley T. Krawczewicz
*Attorney, Agent, or Firm*—John H. Widdowson; Edwin H. Crabtree

[57] ABSTRACT

A corrosion detector for indicating when a transportation vehicle such as an aircraft, train, truck, bus, automobile, or the like, should be washed. The detector indicates the amount of corrosive contamination collected on the vehicle's metal surface. The detector measures the electrical resistance in a chemical solution formed when a water saturated filter paper is placed on the metal surface.

8 Claims, 7 Drawing Figures

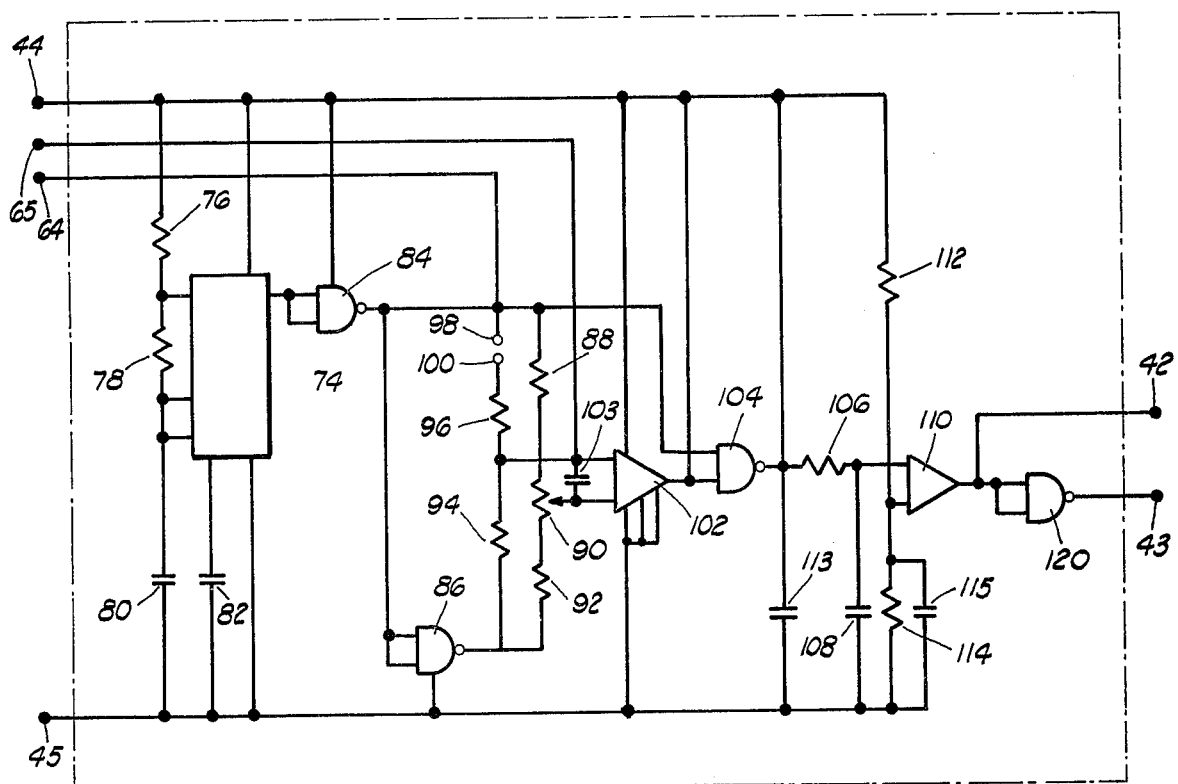
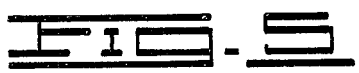
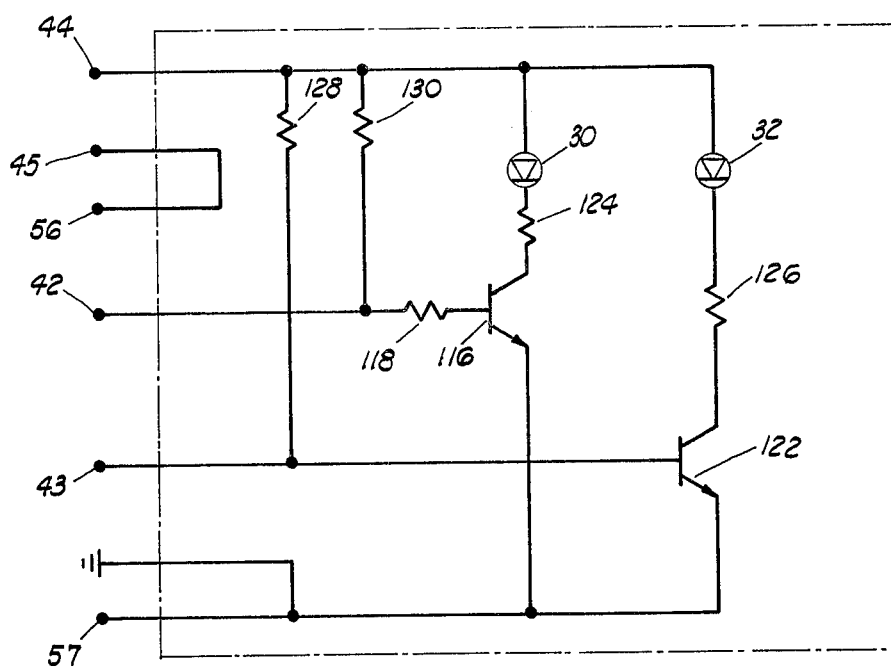

CORROSION DETECTOR

BACKGROUND OF THE INVENTION

This invention relates generally to a device for measuring the amount of corrosive contamination on a metal surface and more particularly, but not by way of limitation, to a corrosion detector for measuring the amount of contaminant in a chemical solution on the metal surface of a vehicle.

Heretofore, there have been various types of testing equipment used for determining the amount of chemical deposition in a solution. Also, there have been various types of meters and methods for determining the amount of corrosion on a metallic surface. These type devices have used electrodes wherein an electrical current is passed between the electrodes in the solution for measuring the resistance of the solution.

In the washing of aircrafts and particularly military aircrafts, an airplane is washed at a scheduled time interval with no regard to whether the airplane needs to be washed or not. This practice is time-consuming and expensive. Also, other types of vehicles are washed at scheduled maintenance time periods with no regard to whether the vehicle needs to be washed. The wash periods have been required at various time periods because the corrosive chemicals such as salt spray, air pollution, or the like, cannot be visually seen on the metal surface. As can be appreciated, the wash periods are more often in coastal areas, industrial locations, and heavily populated areas.

None of the prior art corrosion testing devices and methods have disclosed a simple, yet effective, corrosion detector for determining the amount of contamination collected on a metal surface of a transportation vehicle and when the transportation vehicle is required to be washed.

SUMMARY OF THE INVENTION

The subject invention solves the problem of washing a transportation vehicle at predetermined time intervals and indicates when the vehicle should be washed or not. Also, the detector indicates where high concentrations of corrosive contamination collect on metal surfaces at various location on, for example an aircraft.

The detector is light weight, portable, easy to operate, and quickly tests the amount of contamination on a metal surface. The detector eliminates the cost and time required to wash a vehicle when it is not required.

The detector is calibrated for measuring the resistance of a chemical solution on a filter paper on the metal surface. Light emitting diodes or any other signal or measuring device may be used to indicate when the resistance has reached a predetermined value and the metal surface needs to be washed.

The corrosion detector includes a probe with a pair of electrodes mounted therein. The probe is electrically connected to a battery operated wash meter. A filter paper saturated with water is placed on a metal surface to be tested. The water goes into solution with the corrosive chemicals on the metal surface forming a chemical solution in the filter paper. The probe is placed on top of the filter paper and an electric current is passed from the one electrode through the chemical solution to the other electrode. The wash meter includes means for measuring the resistance of the chemical solution and indicating if the metal surface needs to be washed.

The advantages and objects of the invention will become evident from the following detailed description when read in conjunction with the accompanying drawings which illustrate the preferred embodiments of the invention.

BRIEF DESCRIPTION OF THE DRAWINGS

FIGS. 5 and 6 illustrate a typical electrical circuitry for operating the corrosion detector.

DETAILED DESCRIPTION OF THE DRAWINGS

Figure 1:
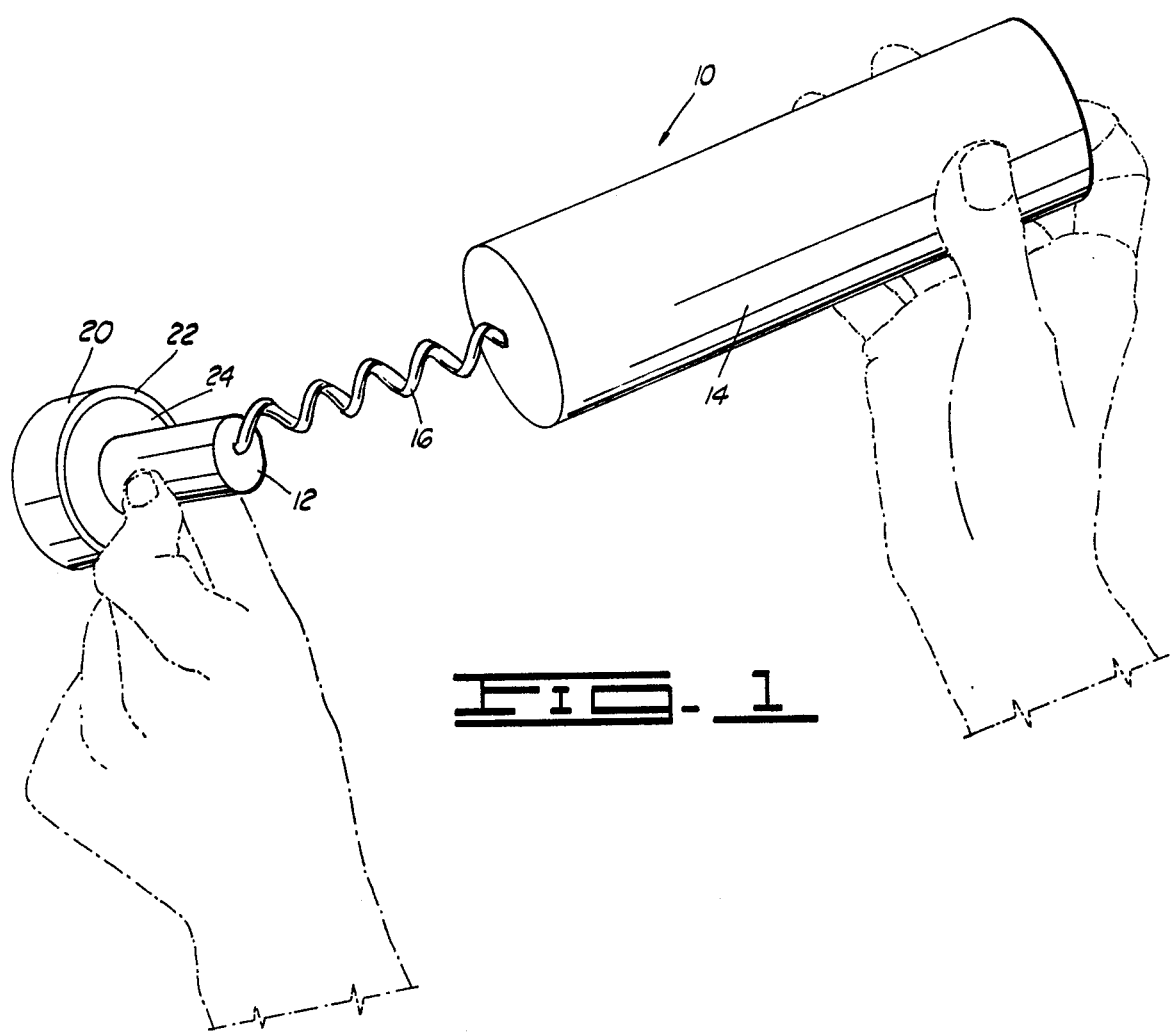
FIG. 1 illustrates a perspective view of a hand held corrosion detector placed on a filter paper disposed adjacent a metal surface.

In FIG. 1, the corrosion detector is designated by general reference numeral 10. The detector 10 includes a probe 12 electrically connected to a battery operated wash meter 14. The probe 12 is connected to the wash meter 14 by a flexible coil 16. The coil 16 allows the probe 12 to be freely moved adjacent a metal surface to be tested. In this illustration, the metal surface to be tested is indicated by an annular shaped metal test piece 20 having an outside surface 22. A filter paper 24 is placed on top of the outside surface 22.

In operation, the filter paper 24 is saturated with a solution of plain tap water. The water combines with the corrosive chemicals on the surface 22 forming a chemical solution. The probe 12 is then placed on top of the filter paper 22 and the battery operated wash meter 14 is turned on to determine the electrical resistance of the chemical solution for indicating whether the metal surface 22 should be washed.

In measuring the resistance of the chemical solution, the greater the concentration of the chemical solution, either basic or acidic, the less resistance is applied by the solution in conducting the electric current. Therefore, a high resistance measurement of the solution would indicate the metal surface need not be washed while a low resistance measurement would indicate the surface needs to be washed. In calibrating and testing the detector 10, a standard solution is used having 2,000 ppm of corrosive chemicals. If the metal surface tested has a chemical solution greater than this standard, then the wash meter 14 will indicate that the surface needs to be washed.

While a filter paper 24 is discussed for holding the chemical solution therein, it is appreciated that other paper products, cloth, or the like could be used for holding the solution to be tested with the probe 12 placed thereon.

If a non-painted metal surface is to be measured, the filter paper 24 must, after allowing 30 to 90 seconds to absorb the surface contamination, be removed and placed on a non-conductive surface to obtain the correct contamination measurement.

The subject invention has been used for indicating the corrosion on the metal surface on the outside of an aircraft. It should be understood that the corrosion detector 10 can also be used equally well for determining when vehicles such as trains, busses, trucks, automobiles or the like are required to be washed. It should also be noted that there are other metal structures requiring a periodic wash where in the past there has been no corrosion detector for determining whether the structure needs to be washed or not. The detector 10 could certainly be used in this type application.

Figure 2:
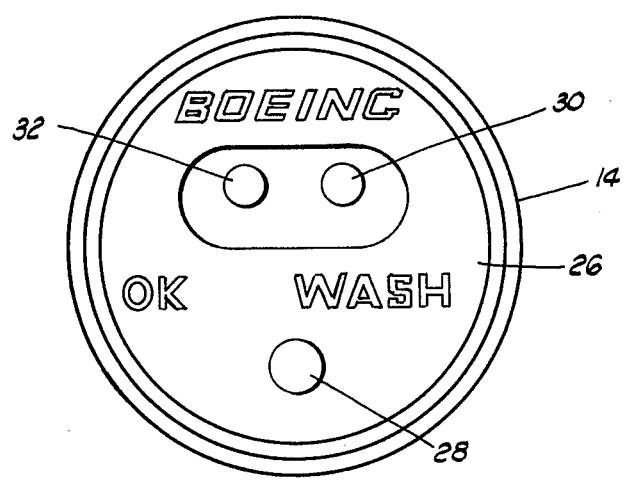
FIG. 2 is a front view of the front panel of the corrosion detector for indicating when the metal surface should be washed.

In FIG. 2, a front panel 26 of the wash meter 14 is illustrated. In the panel 26 is a test switch 28 which is electrically connected to a battery power source inside the meter 14. When the test switch 28 is turned on and the probe 12 is placed on the filter paper 24, the wash meter 14 is electrically calibrated to indicate whether the metal surface 22 needs to be washed. The wash meter 14 indicates that the metal surface 22 needs to be washed by electrically lighting a light emitting diode 30, which for example may be the color red. If the metal surface 22 does not need to be washed, a green light emitting diode 32 lights up indicating that the metal surface 22 is "OK" and is not required to be washed.

Figure 3:
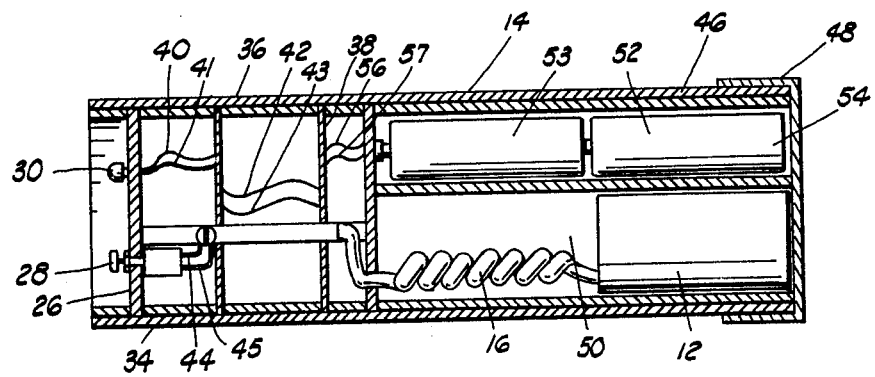
FIG. 3 is a side sectional view of a battery operated wash meter.

In FIG. 3, a side sectional view of the wash meter 14 is illustrated. A front portion 34 of the wash meter 14 includes the front panel 26 with test switch 28 and light emitting diodes 30 and 32. The light emitting diodes 30 and 32 are connected to a printed circuit board 36 and a printed circuit board 38 by electric leads 40, 41, 42, and 43. The test switch 28 is also connected to the circuit boards 36 and 38 by electric leads 44 and 45. The circuitry of the wash meter 14 on the circuit boards 36 and 38 is discussed in detail under FIGS. 5 and 6. The probe 12 is also connected to the circuit boards 36 and 38 by the flexible electrical cable 16. A rear portion 46 of the wash meter 14 includes a cap 48 which may be removed for removing the probe 12 from a storage area 50. Above the probe storage area 50 is a battery storage area 52 for housing penlight batteries 53 and 54, which supply the electrical power to the circuit boards via electrical leads 56 and 57.

Figures 4A, 4B:
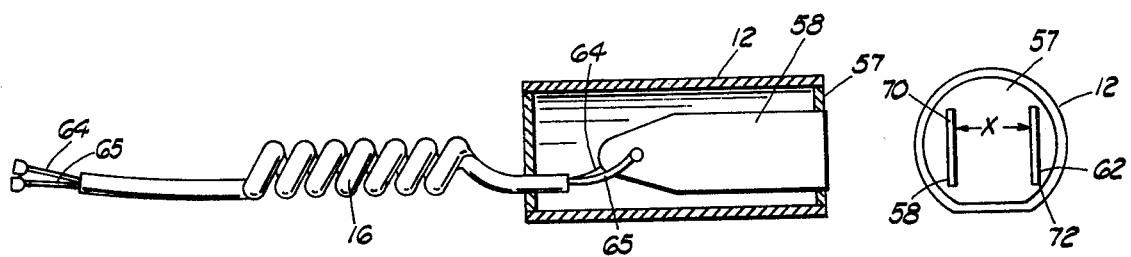
FIG. 4a is a side sectional view of a probe.
FIG. 4b is a front view of the probe.

In FIG. 4a, a side sectional view of the probe 12 is seen with a flat face 57 which is used for placing against the top of the filter 24. In this view, the probe 12 can be seen having an elongated electrode 58 attached to the cable 16 by an electric lead 65. Adjacent the electrode 58 is a second electrode 62 shown in FIG. 4b. The electrode 62 is attached to the cable 16 by an electric lead 64. The cable 16 is attached to the circuit boards 36 and 38 by the leads 64 and 65.

In FIG. 4b, the face 57 of the probe 12 is illustrated wherein the electrodes 58 and 62 include end portions 70 and 72 which are flush with the face 57 of the probe 12. The electrodes 58 and 62 are positioned inside the probe 12 and held in place by a potting compound. The electrodes 58 and 62 are parallel to each other and in a spaced relationship having a dimension X therebetween. The dimension X is a fixed distance between the electrodes 68 and 62, and the dimension X is based on the amount of resistance of the electrical current passed from one electrode through a test sample chemical solution in the filter 22, to the other electrode 62. Once the dimension X is determined, the measurement of the resistance is adjusted by the electrical circuitry discussed under FIGS. 5 and 6.

The wash meter 14 measures the resistance of a chemical solution with the pair of electrodes 58 and 62 in probe 12, by indicating whether the resistance is either above or below a predetermined value and a signal by the use of light emitting diodes 30 and 32. The probe 12, containing the resistant measurement electrodes 58 and 62, forms one leg of a bridge circuit. The other leg of the circuit contains resistors on printed circuit boards 36 and 38 selected to provide a bridge null when the predetermined sample resistance is achieved. A variable resistor is also made a part of the bridge to allow for fine adjustments. For example, the meter 14 is adjusted using a test sample containing 0.2 parts per million of a basic solution. The resistance of this solution is used to adjust the electrical circuitry so that in the testing of the metal surface 22, if the solution's resistance is above the resistance of the test sample, the light emitting diode 32 will indicate that a wash is not necessary. Should the solution be greater than 0.2 parts per million, then the diode 30 will light indicating that the metal surface should be washed.

In the circuitry shown in FIG. 5 and FIG. 6 and attached to the printed circuit boards 36 and 38, the electrical signal source to the bridge is a square wave of approximately 50% duty cycle. The square wave is used to eliminate formation of electrodes or chemical cells within the sample to be measured.

In FIG. 5, electrical leads 44 and 45 from switch 28 are wired to circuit board 36 having an oscillator 74. A resistor 76, a resistor 78, a capicitor 80 and a capicitor 82 are wired to the oscillator 74 for controlling its frequency and an approximate square wave output. The oscillator 74 is connected to intergrated circuit gates 84 and 86 which form invertors and bridge drivers for the square wave signals.

A nulling bridge is formed by a resistor 88, a resistor 90, a resistor 92 and a resistor 94, coupled with the measurement of the resistance across electrodes 58 and 62, connected by leads 64 and 65. A resistor 96 and test points 98 and 100 are included to allow initial adjustment of the bridge null without having to use a standard aqueous salt solution.

The output of the bridge is connected to an intergrated circuit comparator 102. A capacitor 103 is connected to the comparator 102 for stabilizing the input. If the resistance between leads 64 and 65 connected to the electrodes 58 and 62 is less than the preselected value i.e. the resistance of resistor 94, the output of the comparator 102 is a square wave which is 180° out of phase with the output signal of the circuit gate 84. If the resistance between leads 64 and 65 is greater than the output of the comparator 102, then the output of the comparator 102 is a square wave in phase with the output of the circuit gate 84. The output of the comparator 102 and the output of the circuit gate 84 are applied to the input of a "NAND" gate 104. When the outputs are in phase i.e. the sample resistance between the leads 64 and 65 is greater than the reference value, the output of the gate 104 is a square wave. When the two inputs are out of phase, the output of the gate 104 is at a high level. The filter network formed by a resistor 106 and a capacitor 108 filters the output of the gate 104 and drives the input of a second comparator 110.

The input of the comparator 110 will vary from $\frac{1}{2}$ peak output of the filtered square wave from the gate 104 to the peak output of the gate 104. Resistor 112 and resistor 114 define the trip level of the comparator 110 causing it to switch its output to a high state or low state according to whether the output of the gate 104 is a steady high value or a square wave. Capacitors 113 and 115 are connected to the input of the comparator 110 and act to reduce the noise level of the power supply.

The output of comparator 110 drives the base of a transistor 116 through lead 42 shown in FIG. 6 and through a resistor 118. The output of the comparator 110 also drives an invertor 120 which in turn drives the base of a second transistor 122 through lead 43. Transistor 116 drives light emitting diode 30 through resistor 124, while transistor 122 drives the second light emitting diode 32 through a resistor 126. The action of the invertor 110 forces only one of the light emitting diodes 30 and 32 to be illuminated at one time. Resistors 128 and 130 are connected to the input of the transistors 122 and 116 and act as pull up resistors to assure that the input voltage is high enough to turn on the transistors. The light emitting diode 30 connected to transistor 116 will be driven when the resistance of the sample being measured is less than the reference value, indicating that the metal surface needs to be washed. The second light emitting diode 32 connected to transistor 122 will be driven when the resistance of the sample is greater than the reference value.

If the resistance of the sample to be measured changes with temperature, temperature compensation will be required. In this case, a thermistor network can be used to replace resistor 94 in the bridge. This network must have characteristics matching the sample to be measured. To provide maximum temperature compensation, the thermistor must be in close proximity to the electrodes 58 and 62 of the probe 12.

The electrical components shown in FIGS. 5 and 6 have been tested and work satisfactorily in the circuits as described. It is acknowledged that the above circuits are one way of properly wiring the detector 10 and other electrical components will work equally well and fall within the scope of the subject invention.

Changes may be made in the construction or arrangement of the parts or elements of the embodiments as disclosed herein without departing from the spirit or scope of the invention as defined in the following claims.

I claim:

1. A corrosion detector for indicating chemical corrosion on a metal surface and when the surface should be washed, the detector comprising:
    a filter paper for placing on the metal surface to be tested, said filter paper saturated with a solution of water, the water in said filter paper combining with the chemicals on the metal surface to form a chemical solution in said filter paper;
    a probe disposed on top of said filter paper, said probe passing an electrical current through the chemical solution in said filter paper; and
    a battery operated wash meter electrically connected to said probe, said wash meter including means for measuring the electrical resistance of the chemical solution and indicating whether the metal surface should be washed.

2. The detector as described in claim 1, wherein said probe includes a pair of electrodes, said electrodes positioned in a pre-determined spaced relationship from each other in said probe, one of said electrodes passing an electrical current received from said battery operated wash meter through the chemical solution in said filter paper to the other electrode.

3. The detector as described in claim 1, wherein said means for measuring includes electrical circuitry having a light emitting diode electrically wired for indicating when the chemical solution has reached a pre-determined electrical resistance.

4. The detector as described in claim 1, wherein said battery operated wash meter further includes a test switch for electrically turning the electrical power on and off to said wash meter.

5. The detector as described in claim 1, wherein said probe further includes a flexible cable for electrically connecting said probe to said wash meter.

6. The detector as described in claim 1, wherein said battery operated wash meter includes a probe storage area therein for receiving said probe in said wash meter when said probe is not in use.

7. A corrosion detector for indicating chemical corrosion on a metal surface and when the surface should be washed, the detector comprising:
    a filter paper for placing on the metal surface to be tested, said filter paper saturated with a solution of water, the water in said filter paper combining with chemicals on the metal surface to form a chemical solution in said filter paper;
    a probe having a pair of electrodes, said electrodes positioned in a pre-determined spaced relationship from each other in said probe, said probe placed on top of said filter paper, the ends of said electrodes contacting the surface of said filter paper and one of said electrodes passing an electrical current from said electrode through the chemical solution in said filter paper to the adjacent electrode; and
    a battery operated wash meter, said wash meter electrically connected to said electrodes in said probe by a flexible cable, said wash meter including means for measuring the electrical resistance of the chemical solution and indicating whether the metal surface should be washed.

8. The detector as described in claim 7, wherein said means for measuring includes electrical circuitry connected to a test switch and a pair of light emitting diodes, when said switch is turned on, one of said diodes indicates if the electrical resistance of the chemical solution is below a pre-determined value and the other diode indicates the electrical resistance is above the pre-determined value.

* * * * *